US00PP31063P2

(12) United States Plant Patent
Yamada

(10) Patent No.: US PP31,063 P2
(45) Date of Patent: Nov. 12, 2019

(54) ***CALIBRACHOA* PLANT NAMED 'SUNCAL 1544'**

(50) Latin Name: ***Calibrachoa* sp.**
Varietal Denomination: Suncal 1544

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/999,964

(22) Filed: Sep. 4, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821
See application file for complete search history.

*Primary Examiner* — Keith O. Robinson
(74) *Attorney, Agent, or Firm* — C. A. Whealy

(57) ABSTRACT

A new and distinct cultivar of *Calibrachoa* plant named 'Suncal 1544', characterized by its semi-upright and mounding plant habit; vigorous growth habit; freely branching habit; freely flowering habit; long flowering period; large white-colored flowers with yellow-colored centers; and good garden performance.

1 Drawing Sheet

Botanical designation: *Calibrachoa* sp.
Cultivar denomination: 'SUNCAL 1544'.

BACKGROUND OF THE INVENTION

The present invention relates to a new and distinct cultivar of *Calibrachoa* plant, botanically known as *Calibrachoa* sp. and hereinafter referred to by the name 'Suncal 1544'.

The new *Calibrachoa* plant is a product of a planned breeding program conducted by the Inventor in Higashiomi, Shiga, Japan. The objective of the breeding program is to develop new vigorous, semi-upright, mounding and freely branching *Calibrachoa* plants with numerous large and attractive flowers with unique coloration.

The new *Calibrachoa* plant originated from a cross-pollination conducted by the Inventor in Higashiomi, Shiga, Japan in September, 2012 of a proprietary selection of *Calibrachoa* sp. identified as code number C24-269-2, not patented, as the female, or seed, parent with a proprietary selection of *Calibrachoa* sp. identified as code number C23-114-3, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in October, 2013.

Asexual reproduction of the new *Calibrachoa* plant by terminal vegetative cuttings in a controlled greenhouse environment in Higashiomi, Shiga, Japan since November, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncal 1544'. These characteristics in combination distinguish 'Suncal 1544' as a new and distinct *Calibrachoa* plant:

1. Semi-upright and mounding plant habit.
2. Vigorous growth habit.
3. Freely branching habit.
4. Freely flowering habit.
5. Long flowering period.
6. Large white-colored flowers with yellow-colored centers.
7. Good garden performance.

Plants of the new *Calibrachoa* can be compared to plants of the female parent selection. Plants of the new *Calibrachoa* differ primarily from plants of the female parent selection in flower color as plants of the female parent selection have blue-colored flowers. In addition, plants of the new *Calibrachoa* have larger flowers than plants of the female parent selection.

Plants of the new *Calibrachoa* can be compared to plants of the male parent selection. Plants of the new *Calibrachoa* differ primarily from plants of the male parent selection in flower size as plants of the new *Calibrachoa* have smaller flowers than plants of the male parent selection.

Plants of the new *Calibrachoa* can also be compared to plants of *Calibrachoa* sp. 'Suncalho', disclosed in U.S. Plant Pat. No. 21,810. In side-by-side comparisons, plants of the new *Calibrachoa* and 'Suncalho' differ primarily in the following characteristics:

1. Plants of the new *Calibrachoa* are larger than and not as compact as plants of 'Suncalho'.
2. Plants of the new *Calibrachoa* are more freely branching than plants of 'Suncalho'.
3. Plants of the new *Calibrachoa* have smaller leaves than plants of 'Suncalho'.

4. Plants of the new *Calibrachoa* are more freely flowering than plants of 'Suncalho'.
5. Plants of the new *Calibrachoa* have larger flowers than plants of 'Suncalho'.
6. Flower petals of plants of the new *Calibrachoa* have emarginate apices whereas flower petals of plants of 'Suncalho' have apices that are rounded with truncate tendencies.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Suncal 1544' grown in a container.

The photograph at the bottom of the sheet is a close-up view of a typical flowering plant of 'Suncal 1544'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Suncal 1544'.

Parentage:

*Female, or seed, parent*.—Proprietary selection of *Calibrachoa* sp. identified as code number C24-269-2, not patented.

*Male, or pollen, parent*.—Proprietary selection of *Calibrachoa* sp. identified as code number C23-114-3, not patented.

Propagation:

*Type*.—By vegetative terminal cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; white in color.

*Rooting habit*.—Freely branching.

Plant description:

*Plant and growth habit*.—Semi-upright and mounding plant habit; freely branching habit with numerous lateral branches developing per plant; pinching enhances lateral branch development; vigorous growth Nabil.

*Plant height*.—About 23 cm.

*Plant diameter*.—About 78 cm.

Lateral branch description:

*Length*.—About 29 cm.

*Diameter*.—About 1.9 mm.

*Internode length*.—About 1.6 cm.

*Strength*.—Strong.

*Aspect*.—Upright to outwardly.

*Texture*.—Densely pubescent; rough.

*Color*.—Close to 144A.

Leaf description:

*Arrangement*.—Alternate, simple.

*Length*.—About 3.5 cm.

*Width*.—About 1.3 cm.

*Shape*.—Elliptic.

*Apex*.—Broadly acute.

*Base*.—Attenuate.

*Margin*.—Entire.

*Texture, upper and lower surfaces*.—Densely pubescent; rough.

*Venation pattern*.—Pinnate; reticulate.

*Color*.—Developing leaves, upper surface: Close to 138A. Developing leaves, lower surface: Close to 138B. Fully expanded leaves, upper surface: Close to 137B; venation, close to 144C. Developing and fully expanded leaves, lower surface: Close to 137D; venation, close to 145C.

*Petioles*.—Length: About 4.6 mm. Diameter: About 2.1 mm. Texture, upper and lower surfaces: Pubescent. Color, upper and lower surfaces: Close to 144B.

Flower description:

*Flower arrangement and habit*.—Single salverform flowers arising from upper leaf axils; freely flowering habit with usually about 280 flowers developing per plant; flowers face upright to outwardly.

*Fragrance*.—None detected.

*Natural flowering season*.—Early flowering, habit, plants of the new *Calibrachoa* initiate and develop flowers about three to four weeks after planting; long flowering period, flowering naturally commences during the spring and plants flower continuously throughout the summer until late autumn in Japan.

*Flower longevity*.—Individual flowers last about seven to ten days on the plant; flowers not persistent.

*Flower diameter*.—About 5 cm.

*Flower length (depth)*.—About 1.3 cm.

*Throat diameter*.—About 9 mm.

*Tube length*.—About 1.7 cm.

*Tube diameter, base*.—About 3.3 mm.

*Flower buds*.—Length: About 2.5 cm. Diameter: About 6.8 mm. Shape: Cylindrical. Color: Close to 4C.

*Corolla*.—Arrangement: Five petals fused at the base and opening into a flared trumpet. Petal length from throat: About 2.1 cm. Petal width: About 2 cm. Petal shape: Roughly spatulate. Petal apex: Emarginate. Petal margin: Entire; slightly undulate. Petal texture, upper and lower surfaces: Smooth, glabrous. Throat texture: Smooth, glabrous. Tube texture: Smooth, glabrous. Color: Petal, when opening, upper surface: Close to NN155C. Petal, when opening, lower surface: Close to NN155D. Petal, fully opened, upper surface: Close to NN155D; venation, faint, close to 1A; color does not change with development. Petal, fully opened, lower surface: Close to NN155D; venation, close to 144C; color does not change with development. Throat: Close to 1C; proximally, close to 9B; venation, faint, close to NN144B. Tube: Close to 3B and 3D; venation, close to 144C.

*Calyx*.—Arrangement: Star-shaped tubular calyx tube with five sepals in a single whorl and fused at the base. Sepal length: About 1.1 cm. Sepal width: About 2.8 mm. Sepal shape: Lanceolate. Sepal apex: Acute. Sepal margin: Entire. Sepal texture, upper and lower surfaces: Pubescent. Sepal color: Immature and mature, upper surface: Close to 138A. Immature and mature, lower surface: Close to 138A.

*Peduncles*.—Length: About 2 cm. Diameter: About 0.8 mm. Angle: Upright to outwardly. Strength: Strong. Texture: Pubescent. Color: Close to 144A.

*Reproductive organs*.—Stamens: Quantity: Five per flower. Filament length: About 8.6 mm. Filament color: Close to 145C. Anther shape: Ellipsoidal. Anther size: About 1.6 mm by 1.2 mm. Anther color: Close to 4B. Pollen amount: Moderate. Pollen color: Close to 4A. Pistils: Quantity: One per flower. Pistil length: About 1 cm. Style color: Close to 144C. Stigma shape: Transversely ellipsoidal. Stigma color: Close to 144B. Ovary color: Close to 145B.

*Seeds and fruits*.—To date seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: To date, plants of the new *Calibrachoa* have not been observed to be resistant to pests and pathogens common to *Calibrachoa* plants.

It is claimed:

1. A new and distinct *Calibrachoa* plant named 'Suncal 1544' as illustrated and described.

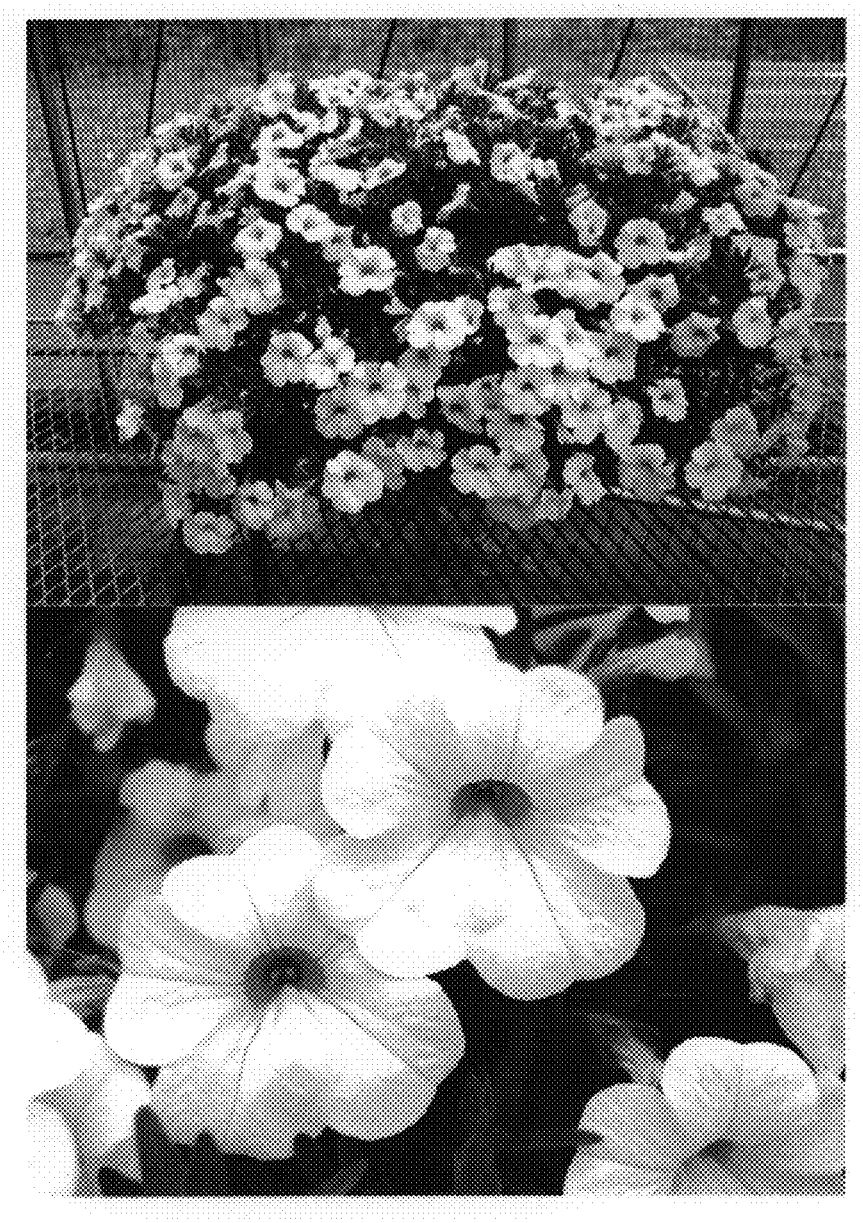

* * * * *